United States Patent
Mah

(10) Patent No.: US 10,959,451 B2
(45) Date of Patent: Mar. 30, 2021

(54) SUCRALEZ COMPOSITION

(71) Applicant: DuraScience Inc., New York, NY (US)

(72) Inventor: James Nitit Mah, New York, NY (US)

(73) Assignee: Durascience, Inc., New York, NY (US)

( * ) Notice: Subject to any disclaimer, the term of this patent is extended or adjusted under 35 U.S.C. 154(b) by 32 days.

(21) Appl. No.: 16/679,286

(22) Filed: Nov. 10, 2019

(65) Prior Publication Data

US 2020/0068937 A1  Mar. 5, 2020

(51) Int. Cl.

| | | |
|---|---|---|
| *A61K 36/00* | (2006.01) |
| *A23L 33/105* | (2016.01) |
| *A61K 36/06* | (2006.01) |
| *A61K 36/8962* | (2006.01) |
| *A61K 36/55* | (2006.01) |

(52) U.S. Cl.
CPC ............ *A23L 33/105* (2016.08); *A61K 36/06* (2013.01); *A61K 36/55* (2013.01); *A61K 36/8962* (2013.01)

(58) Field of Classification Search
CPC ...................................................... A61K 36/00
USPC ........................................................... 424/725
See application file for complete search history.

(56) References Cited

U.S. PATENT DOCUMENTS

2018/0280430 A1* 10/2018 Bortz ................... A61K 36/064

* cited by examiner

*Primary Examiner* — Michael V Meller

(57) ABSTRACT

In an embodiment, a nutritional supplement composition is provided. The nutritional supplement composition is provided including a combination of 45 mg of flaxseed extract from the *Linum usitatissimum* strain, 25 mg of garlic extract *Allium sativum* strain and 40 mg shitake extract from the *Lentinus edodes* strain. The nutritional supplement is in the form of a compound known as SUCRALEZ™.

2 Claims, No Drawings

SUCRALEZ COMPOSITION

BACKGROUND

In the past, we commonly used all parts of natural foods when we consumed a meal. Human eating patterns naturally accessed nutrients available from what was eaten and very little nutrients were wasted as a result. For example, when eating fish, the muscular parts of the fish were consumed along with other parts such as connective tissue. When eating plants, the edible portion of the plant was consumed in its entirety. Our bodies would then filter out what was not consumable, such as the outer shell of a kernel of corn for example. As this occurred, our bodies would extract what nutrients could be found in the food to sustain and grow the human form. This allowed use of local foods to provide nutrients which were available, but was somewhat limited in that foods not available locally could not be used in most cases. Over time, we learned to travel and to ship food from where it was produced to where it could be consumed. Additionally, we learned to prepare foods, removing portions of the food which were either inedible, or undesirable. Removing the inedible parts typically provided some benefit, while parts that were simply undesirable sometimes held valuable ingredients.

Flax (*Linum usitatissimum*), also known as common flax or linseed, is a member of the genus *Linum* in the family Linaceae. It is a food and fiber crop cultivated in cooler regions of the world.

Garlic (*Allium sativum*) is a species in the onion genus, *Allium*. Garlic is native to Central Asia and northeastern Iran, and has long been a common seasoning worldwide, with a history of several thousand years of human consumption and use. China produces some 80% of the world supply of garlic, and it is produced in a variety of areas worldwide at this time.

The shiitake, *Lentinula edodes*, is an edible mushroom native to East Asia, which is cultivated and consumed in many Asian countries. It is considered a medicinal mushroom in some forms of traditional medicine Shiitake's native land is Asia with a great presence in China. It has been held with great importance in Japan too. Its name, Shiitake, is Japanese, where 'Shii' is the name of the tree that usually hosts the mushroom. The tree belongs to the Birch family. 'Take' means the mushroom fruit. Despite its preferences above, Shiitake is very adaptable and can grow anywhere. In the US, for instance, people grow them in simple greenhouses, converted chicken houses, under tree shades outside, and virtually anywhere.

SUMMARY OF THE INVENTION

A nutritional supplement composition is provided including a flaxseed extract from the *Linum usitatissimum* strain, garlic extract *Allium sativum* strain and shitake extract from the *Lentinus edodes* strain. The nutritional supplement is in the form of a compound known as SUCRALEZ™.

The foregoing, and other features and advantages of various embodiments of the invention, will be apparent from the following, more particular description of the embodiments of the invention, any accompanying drawings, and the claims.

DETAILED DESCRIPTION

A composition is provided as SUCRALEZ™. The specific embodiments described in this document represent exemplary instances of the present invention, and are illustrative in nature rather than restrictive.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments.

*Linum usitatissimum* finds its way into folk remedies for boils, bronchitis, burns, cancer, carbuncles, cold, conjunctivitis, corns, coughs, diarrhea, gonorrhea, gout, inflammation, intoxication, labor, rheumatism, scalds, sclerosis, sores, spasms, swellings, and tumors.

One study of research published between 1990 and 2008 showed that consuming flaxseed or its derivatives may reduce total and LDL-cholesterol in the blood, with greater benefits in women and those with high cholesterol.

A meta-analysis has shown that consumption of flaxseed contributed to reduced body weight, body mass index (BMI), and waist circumference for persons with high BMIs. Another meta-analysis has shown that consumption of flaxseed for more than 12 weeks produced small reductions in systolic blood pressure and diastolic blood pressure.

Flaxseed contains lipid (40%), protein (21%), dietary fiber (28%), ash (4%), and other soluble components such as sugars, phenolic acids, and lignans (ca 6%). The oil content in flaxseed represents between 29 and 45% of the seed depending on the cultivar, location, and agroclimatic conditions according to one study. The main nutritional advantage of flaxseed oil is related to the high level of ALA in the oil (50%-60%). About 20% of the flaxseed is a mucilagenous hull. Flaxseed mucilage appears to be made up of gum-like polysaccharides containing acidic (54.5% rhamnose and 23.4% galactose) and neutral arabinoxylan (62.8% xylose). Flaxseed contains about 1%-2% total phenolic compounds, of which the lignan secoisolariciresinol diglucoside (SDG) is a major component. SDG is present in the seed as a mixture of oligomers with hydroxymethylglutaric acid having an average molecular weight of 4000 Da. A number of bioactivities are claimed for SDG including antioxidant and estrogenic/oestrogenic effects, leading to health benefits with respect to cardiovascular diseases, diabetes, and menopause. Flaxseed has also been used for constipation.

*Allium sativum* L. (garlic), which is a species of the onion family, Alliaceae, is one of the most used plants in traditional medicine worldwide. More than 200 chemicals with diverse properties have been found in garlic extracts. Several garlic compounds were suggested to be efficient in improving various pathologies including certain types of cancer. Garlic and its compounds were found to have notable antioxidant properties. Garlic therapeutic potential has also been studied in several inflammatory diseases such as allergic-airway inflammation, inflammatory bowel disease, arthritic rheumatism, and atherosclerosis. Furthermore, garlic was found to be able to maintain the immune system homeostasis and to exhibit beneficial effects on immune cells especially through regulation of proliferation and cytokine gene expression.

Garlic (*Allium sativum*) has been marketed for antimicrobial and antiparasitic properties. Garlic's potentially active components include a number of organosulfur compounds (e.g., allicin) as well as a variety of nonsulfur compounds including steroid aponins and various organoselenium compounds. The high sulfur content of garlic has been theorized to help cleanse the blood. In the horse industry, garlic is primarily fed for purported insect repellent effects. Respiratory health benefits (alterations in the physical properties of mucus) have also been claimed.

Garlic has been used for hardening of the arteries (atherosclerosis) and high blood pressure (hypertension). Garlic has also been used to prevent tick bites.

*Lentinus edodes* is used medicinally for diseases involving depressed immune function (including AIDS), cancer, environmental allergies, fungal infection, frequent flu and colds, bronchial inflammation, heart disease, hyperlipidemia (including high blood cholesterol), hypertension, infectious disease, diabetes, hepatitis and regulating urinary inconsistencies.

Studies of shiitake extracts suggest antiproliferative, immunostimulatory, hepatoprotective, antimutagenic, and anticaries effects in vitro and in mice. Studies of shiitake indicated that the mushroom is low in sodium, low in glucose and is a rich source of fibre. Hence, Shiitake can be helpful for diabetics, for example.

In Japan, Shiitake has been used as a natural treatment of cancer because of its complex carbohydrate, Lentinan. It is also a source of selenium, an antioxidant that is believed to prevent cancer. The mushroom is credited with lowering serum cholesterol levels by 12% through eritadenine. Eritadenine is a compound contained in the mushroom.

Shiitake's healing properties are also reflected in its anti-viral strengths. It is speculated that once metabolised, the glucan based compound therein is able to fight the influenza virus, bacterial infection, and other infectious elements such as cancerous cells. Some physicians are also using it as injectable medication to fight cancer.

The benefit of the composition includes restoring and enhancing cells. Our cells constantly deteriorate in daily life. If there is no support to restore the deterioration, cellular damage will affect the body functions. SUCRALEZ™ composition is a supplementary factor that can restore the cells to the body balance without drug and substance usage. When cells are restored, in the next process, SUCRALEZ™ composition may accordingly boost cell strength, equivalent to increasing the effectiveness and the number of cells, while maximizing physical and mental abilities After the cellular restoration and boosting the cell strength, the next challenge is the protection to maintain the long-lasting quality of the cells. SUCRALEZ™ dietary supplement may help to protect and delay the cellular deterioration. This will also result in improving the immune system, as the immune system no longer needs to activate against inflammation or other forms of deterioration. When the cell functions are systematically restored, boosted and protected, SUCRALEZ™ dietary supplement may directly enhance physical and mental capacity to go beyond limits at each age and to live life fully as the pace of life requires a strong response to maintain youth and vigor.

The health benefits of SUCRALEZ™ are also potentially of value to children, and help to develop the strength of new cells and protect cells from early deterioration. Both are beneficial to the development of body, intelligence, memory, and positive emotions. The physical results may include i) restore cells for normal growth in each stage, ii) recover from illness, iii) build muscle, v) boost the immune system, vi) reduce the risk of the incidence of disease, vii) promote growth to maximum effectiveness, viii) adjust height, ix) improve body growth, x) efficient immunity and xi) increase energy. The wound and injury healing properties are potentially of particular assistance to children, as the nutrients provided assist specifically with structures often injured in sports or other childhood activities.

The composition also helps to restore the old damaged cells, repair damaged body tissues, delay the cellular deterioration, inhibit free radicals, and help the process of skin cell renewal in adults for glowing skin and younger appearance. Providing building blocks as previously mentioned contribute to enhancing balance, reducing exhaustion from stress and demands of healing, improving concentration and work efficiency, reducing healing time and longer term pain, and boosting the immune system to stay healthy Physical results may also include: a radiant and vibrant skin, younger appearance; reducing fatigue at work; restoring the reproductive system; refreshing the body; boosting the immune system; protecting against free radical formation; and preventing premature aging.

The compounds are typically dried and ground or milled to small particles, and subsequently combined in the desired ratio. The combination may remain as a powder to be added to food or pressed in a tablet. Alternatively, the compounds may be mixed in an aqueous or other liquid solution and thereby provided in liquid form.

In an embodiment, a preferred dosage, the total compound blended is 110 mg, pressed into a single tablet. The compound may be sold under the SUCRALEZ™ name. The dosage may include a combination of 45 mg of flaxseed extract from the *Linum usitatissimum* strain, 25 mg of garlic extract *Allium sativum* strain and 40 mg shitake extract from the *Lentinus edodes* strain. However, other ratios of the ingredients may be provided, and smaller or larger dosages may be used for particular applications.

Study of SUCRALEZ™ Effectiveness

A study of users of a trial formulation was conducted. The study focused primarily on diabetic considerations, but also considered other possible results. Participants reported the following results:

Ninety-two percent (92%) of participants reported decreased blood sugar levels, with a response of typically a twenty-five percent (25%) decrease in blood sugar level as a measured result.

Eighty-four percent (84%) of participants reported reduced intestinal sugar absorption, with a measured result of twenty-five percent (25%) reduction in 2-hour postprandial sugar level.

Approximately eighty percent (80%) of participants reported better results on metabolic control. The participants reported a measured result of a thirty percent (30%) reduction in serum triglyceride. Participants also reported a measured result of a twenty percent (20%) increase in serum HDL (high density lipoprotein).

Eighty percent (80%) of participants reported better cardiovascular control. The participants reported a typical fifteen percent (15%) decrease in blood pressure.

Eighty-six percent (86%) of participants also reported decreases in abdominal obesity. Participants saw a typical thirty percent (30%) reduction in abdominal size.

Approximately eighty percent (80%) of participants reported a better microbacterial environment in the intestine, with a typical measured result of a ninety percent (90%) better microbacterial balance in the intestine.

Approximately eighty-four percent (84%) of participants reported a decrease in diabetic complications. Participants showed as much as ninety percent (90%) reduction in diabetic foot ulcer conditions. Participants also showed as much as an eighty percent (80%) decrease in incidence of diabetic foot numbness.

Eighty-seven percent (87%) of participants reported better resistance to diabetic cravings. The participants reported an eighty percent (80%) decrease in incidence of need for an extra meal per day.

One skilled in the art will appreciate that although specific examples and embodiments of the system and methods have been described for purposes of illustration, various modifications can be made without deviating from present invention. For example, embodiments of the present invention may be applied to many different types of databases, systems and application programs. Moreover, features of one embodiment may be incorporated into other embodiments, even where those features are not described together in a single embodiment within the present document.

The invention claimed is:

1. A tablet consisting essentially of a flaxseed extract, a garlic extract, and a shiitake extract.

2. The tablet of claim 1, wherein the flaxseed extract is in an amount of 45 mg, the garlic extract is in an amount of 25 mg and the shiitake extract is in an amount of 40 mg.

* * * * *